United States Patent
Farron

(10) Patent No.: US 10,016,361 B2
(45) Date of Patent: Jul. 10, 2018

(54) PH CHANGE IN THE VAGINA AS A CONTRACEPTIVE

(71) Applicant: Francoise Farron, La Jolla, CA (US)

(72) Inventor: Francoise Farron, La Jolla, CA (US)

(*) Notice: Subject to any disclaimer, the term of this patent is extended or adjusted under 35 U.S.C. 154(b) by 0 days.

(21) Appl. No.: 14/572,740

(22) Filed: Dec. 16, 2014

(65) Prior Publication Data

US 2016/0113869 A1 Apr. 28, 2016

Related U.S. Application Data

(60) Provisional application No. 62/068,088, filed on Oct. 24, 2014.

(51) Int. Cl.
| | |
|---|---|
| A61K 9/02 | (2006.01) |
| A61K 47/02 | (2006.01) |
| A61K 31/194 | (2006.01) |
| A61K 31/201 | (2006.01) |
| A61K 9/00 | (2006.01) |
| A61K 33/00 | (2006.01) |

(52) U.S. Cl.
CPC .............. *A61K 9/02* (2013.01); *A61K 9/0034* (2013.01); *A61K 31/194* (2013.01); *A61K 31/201* (2013.01); *A61K 33/00* (2013.01); *A61K 47/02* (2013.01)

(58) Field of Classification Search
None
See application file for complete search history.

(56) References Cited

U.S. PATENT DOCUMENTS

| | | | |
|---|---|---|---|
| 4,368,186 A | 1/1983 | Vickery | |
| 4,588,581 A | 5/1986 | Schmolka | |
| 4,665,096 A | 5/1987 | Oraa | |
| 4,670,256 A | 6/1987 | Doran | |
| 4,981,686 A | 1/1991 | Hardy | |
| 5,326,556 A * | 7/1994 | Barnet | A61K 8/042 424/400 |
| 5,958,461 A | 9/1999 | Larsen | |
| 6,830,557 B2 * | 12/2004 | Paul | A61O 9/02 604/153 |
| 7,521,064 B2 | 4/2009 | Saxena | |
| 8,394,840 B2 | 3/2013 | Chong | |
| 2009/0320855 A1 | 12/2009 | Shihata | |
| 2012/0263667 A1 | 10/2012 | Zhou | |

FOREIGN PATENT DOCUMENTS

| | | | |
|---|---|---|---|
| KR | 20110057843 A | * | 6/2011 |
| KR | 20110057843 A | * | 6/2011 |

OTHER PUBLICATIONS

US 5,735,870, 03/1998, Thoene (withdrawn)
Lee et al., English Traslation of KR 20110057843 abstract only, Jun. 1, 2011.*
Lee et al., English Traslation of Kr 20110057843 abstract only, Jun. 1,2011.*
Brodie, J. F., "Contraception and Abortion in Nineteenth-Century America", Cornell University, 1994, p. 75.*
Thompson, Jr. "Spermicide: The Pros and Cons", www.everydayhealth.com, Jul. 16, 2009.*

* cited by examiner

*Primary Examiner* — Carlos A Azpuru
*Assistant Examiner* — Casey S Hagopian
(74) *Attorney, Agent, or Firm* — Kane Kessler, P.C.; Barry E. Negrin

(57) ABSTRACT

Human sperm is mobile only in a slightly acidic environment which is the normal state of the human vagina. Soap is a very basic material; introduction of a small amount of soap into the vagina before intercourse will raise the pH, a condition which causes the sperm to coagulate into a ball, that exits the vagina upon simply rinsing with water. The present invention is a composition of soap, water, and other natural materials that can be used as a vaginal suppository.

2 Claims, No Drawings

PH CHANGE IN THE VAGINA AS A CONTRACEPTIVE

RELATED APPLICATIONS

This application claims the benefit of U.S. Provisional Application 62/068,088, dated Oct. 24, 2014, whose contents are included by reference.

FIELD OF THE INVENTION

This invention relates to compositions and methods for preventing conception in sexually active females. The compositions of the present invention, when used within the vagina during sexual intercourse, physically trap and inactivate spermatozoa contained in ejaculate that may be deposited within the vagina.

BACKGROUND OF THE INVENTION

Birth control devices—including barrier methods and vaginal contraceptives—are currently available over the counter. For example, condoms can help prevent transmission of sperm during intercourse.

There are chemical barriers as well. For example, Non-oxynol-9, which is a nonionic detergent with strong surfactant properties, acts by killing or otherwise immobilizing spermatozoa. It is a potent cytotoxic agent which tends to nonspecifically disrupt cell membranes. As a consequence, Nonoxynol-9 can injure vaginal/cervical epithelial and other cells at very low concentrations.

Other spermicides have similar undesirable side-effects. There is a need for a more natural and less disruptive spermicide that has few if any harmful side effects.

The primary means of birth control in the United States is "The Pill", or oral hormonal contraceptives. Studies report that about 50% of women who begin using oral contraceptives discontinue use within the first six to twelve months due to side effects.

There are labels on Pill packaging warning that the pill substantially increases women's risks to many health problems, some of which are potentially very serious. Oral contraceptives increase a woman's risk of heart attacks, strokes, blood clots, depression, sleep disorders, anemia, low energy, migraine headaches, vaginal yeast infections, diabetes, a weakened immune system, giving birth to an infant with birth defects, and cancers in the uterus, colon and breast.

The hormones used in "the Pill," are synthetic, structurally altered as compared to naturally occurring hormones. These derivatives actually deplete the body of a large number of nutrients, mostly vitamins, antioxidants and so-called "trace elements,"—minerals that are essential to one's health, but needed only in tiny quantities, or "trace amounts."

SUMMARY OF THE INVENTION

This invention is comprised of compositions and methods which are contraceptive during sexual activity.

Human sperm is known to be mobile only in an acidic environment, which is the normal state of the human vagina. Fertilization occurs in the Fallopian tubes; thus, in order for fertilization to occur, the sperm has to travel up into the Fallopian tubes, i.e. the sperm has to be motile.

Introduction of a small amount of the invention into the vagina immediately before intercourse will raise the pH in the vagina sufficiently to cause ejaculate present to coagulate into a clump that should exit the vagina as soon as the woman assumes a vertical position. Rinsing with water is recommended to help the pH to return to its normal, slightly acidic value.

The method of this invention comprises the application of the composition of the invention within the vagina prior to engaging in sexual activity. The composition of this invention act as a vaginal contraceptive and has fewer side effects than conventional vaginal contraceptives.

Human sperm is mobile only in a slightly acidic environment. When the invention is introduced into the vagina before sexual intercourse, it causes the entire ejaculate to coagulate into a firm clump that exits the vagina when the woman resumes an erect position, or urinates. A rinse with water is recommended to help restore the pH to an acidic value. The present invention is a composition of soap, water, and other natural materials that can be used as a vaginal suppository.

DETAILED DESCRIPTION

The preferred embodiment of the present invention is comprised of a solution of soap, water, and other substances to raise the pH of the vaginal area to a higher value.

Composition of the product:
  Distilled water—50%
  Potassium hydroxide—15%
  Coconut oil—20%
  Palm oil, oleic fatty acid—6%
  Citric Acid enough to adjust the pH of the composition
  Lavender fragrance—1%
  Distilled water to make 100%.
All percentages are by weight.

Saponification is accomplished by mixing the above ingredients in 'the cold process', which involves the steps of mixing the oils at a low temperature, no more than 110 degrees Fahrenheit, mixing the potassium hydroxide solution with water to form a solution, adding the potassium hydroxide solution to the oil mixture at room temperature, then adding the citric acid and fragrance to bring the mixture to the desired pH.

Water is added to bring the combined mixture to the desired consistency.

Note that the invention can be practised with other formulations that produce a gelatinous, soapy substance with an alkaline pH in the desired range. Original studies done on this method used Johnson's Baby Soap® as the substance.

The present invention is used by obtaining the recommended amount of the invention in the hand and then, using the fingers, inserting said invention into the vaginal opening, then engaging in sexual activity. The vaginal area can then be washed out and any semen that had been deposited in said opening would be completely cleaned away.

The presence of the invention in the human vagina changes the acidity of the vaginal area radically. Human sperm is mobile only in a slightly acidic environment which is the normal state of the human vagina. Introduction of the invention into the vagina before intercourse will raise the pH, which forces any sperm present to coagulate into a ball which can later be washed out with water.

The invention is not a spermicide and no spermicidal function is intended or obtained. The invention if used properly immobilizes sperm physically and chemically with an elevated pH of the vagina, using natural ingredients to minimize irritation.

This invention has other applications, potentially, and one skilled in the art could discover these. The explication of the features of this invention does not limit the claims of this application; other applications developed by those skilled in the art will be included in this invention.

What is claimed is:

1. A method of using a mildly alkaline soap-like gelatinous mixture as a non-spermicidal contraceptive, comprising the steps of:
   a. selecting the mildly alkaline soap-like mixture with the desired gelatinous consistency and chemical pH,
   b. obtaining an amount of the gelatinous mixture in the hand, then
   c. using the fingers, inserting said gelatinous mixture into the human vaginal opening immediately prior to intercourse, then
   d. engaging in sexual activity, wherein any male ejaculate contacting the inserted gelatinous mixture will coagulate and thereby immobilize sperm contained therein, then
   e. washing out any balled-up semen trapped in the mixture that had been deposited in said vaginal opening.

2. A method as in claim 1 using a mildly alkaline soap-like gelatinous mixture comprising
   a. Distilled water 50%,
   b. Potassium hydroxide 15%,
   c. Coconut oil 20%
   d. Oleic fatty acid 6%,
   e. Lavender fragrance 1%,
   f. Citric Acid to adjust the pH of the mixture, and
   g. sufficient additional distilled water to make 100%,
the percentages of components by weight, said mixture achieving a gelatinous consistency.

* * * * *